United States Patent [19]

Hasson et al.

[11] Patent Number: 5,261,917

[45] Date of Patent: Nov. 16, 1993

[54] SUTURE TYING FORCEPS WITH A PLURALITY OF SUTURE HOLDERS AND METHOD OF TYING A SUTURE

[76] Inventors: Harrith M. Hasson, 2043 N. Sedgwick, Chicago, Ill. 60614; Carlos A. Rotman, 1799 Shore Acres, Lake Bluff, Ill. 60044

[21] Appl. No.: 838,359

[22] Filed: Feb. 19, 1992

[51] Int. Cl.⁵ .............................................. A61B 17/00
[52] U.S. Cl. .................................... 606/139; 606/148; 606/151; 606/205; 606/206; 606/207; 606/208
[58] Field of Search ............... 606/205, 206, 207, 208, 606/209, 148, 120, 139, 151

[56] References Cited

U.S. PATENT DOCUMENTS

| 848,126 | 3/1907 | Roosevelt | 606/205 X |
| 1,513,367 | 10/1924 | Brix | 606/208 X |
| 4,635,638 | 1/1987 | Weintraub et al. | 606/205 X |
| 5,147,373 | 9/1992 | Ferzli | 606/207 |

FOREIGN PATENT DOCUMENTS 1321409  7/1987  U.S.S.R. .................. 606/207

Primary Examiner—Stephen C. Pellegrino
Assistant Examiner—Jeffrey A. Schmidt
Attorney, Agent, or Firm—Wood, Phillips, VanSanten, Hoffman & Ertel

[57] ABSTRACT

An instrument for facilitating the tying of a suture during a surgical procedure. The instrument has a body with a first structure for releasably holding a first portion of a suture and a second structure, spaced from the first holding structure, for releasably holding a second portion of the suture. Actuating structure is provided to selectively cause the first holding structure to hold and release the first portion of the suture and causing the second holding structure to hold and release the second portion of the suture.

28 Claims, 3 Drawing Sheets

SUTURE TYING FORCEPS WITH A PLURALITY OF SUTURE HOLDERS AND METHOD OF TYING A SUTURE

BACKGROUND OF THE INVENTION

1. Field of the Invention

The present invention is directed to a medical instrument, and, more particularly, to an instrument for facilitating the tying of a suture, as during microsurgical and laparoscopic procedures. The invention is also directed to a method of tying a suture using the inventive instrument.

BACKGROUND ART

The tying of sutures during microsurgical and laparoscopic procedures often is a difficult process that may lengthen operating time inordinately. Normally, a needle with an attached suture is passed through two opposing tissue surfaces to be bound, leaving a terminal short suture segment on one side and a proximal long suture segment terminating with the needle on the other side. The opposite suture ends are then knotted using tying techniques which require a number of throws of the suture ends about each other. Numerous difficulties can arise in tying such sutures.

During the first throw of the suture, the free short end of the suture may slip out of the tissues with a slight miscalculation of hand movements, necessitating a repetition of the process. Also, between throws the first half of the tie may loosen unacceptably if appropriate tension is not maintained on the suture line. Further, if the surgeon applies reasonable tension on one suture limb against the other to overcome loosening of the tie, the suture may become frayed or break if the angle of pull is inappropriate. These problems are exaggerated still further during laparoscopic procedures in which the suturing process is carried out at some distance from the controlling hand, such that the effect of any false hand movement is amplified.

One technique that has been devised by Dr. Harrith M. Hasson, one of the inventors herein, to facilitate the tying of sutures involves making a knot by passing the needle of a suture through a noose loop formed near a terminal end of the suture. The technique prevents inadvertent slippage of the suture's free short end through tissues, replaces the difficult first throw with a simple passage of a needle through a noose and equalizes the amount of tension applied on the suture as it slides smoothly within the noose. This technique is described extensively in an article entitled "Suture Loop Techniques to Facilitate Microsurgical and Laparoscopic Procedures", Journal of Reproductive Medicine, 1987, 32:765=767, authored by the one inventor herein.

Existing surgical instruments provide limited utility in performing suture loop techniques during microsurgical procedures, and have even less utility in laparoscopic suture tying applications. To form a loop and a resulting tie, it is necessary to grasp a terminal portion of the suture in which the loop is to be formed, to form a suture loop in the loose suture using a second instrument and then grasp a proximate suture portion to be drawn through the loop and tightened against the joined tissue. While this technique conceivably can be performed by a single skilled surgeon working with a pair of conventional forceps and his/her hands, the inordinate degree of manipulation of the suture portions can prove quite cumbersome. During laparoscopic procedures, in which the entire suture tying procedure takes place within a patient's body cavity, the surgeon cannot utilize his/her hands and must rely entirely on the use of instruments. Existing instruments do not conveniently permit the intricate manipulation required for suture loop techniques during laparoscopic surgical procedures.

SUMMARY OF THE INVENTION

The present invention is specifically directed to overcoming the above-enumerated problems in a novel and simple manner.

According to the invention, an instrument is provided for facilitating the tying of a suture during a surgical procedure. The instrument has a body with a first structure for releasably holding a first portion of a suture and a second structure, spaced from the first holding structure, for releasably holding a second portion of the suture. Actuating structure is provided to selectively cause the first holding structure to hold and release the first portion of the suture and causing the second holding structure to hold and release the second portion of the suture.

While the above structure has utility in potentially a number of different applications, it is particularly adaptable to tying a suture, as to close an incision. More particularly, the invention comprehends the tying of a suture that is directed, as by a needle, through tissue on opposite sides of an incision therein so that a first end of the suture extends from one part of the tissue and a second end extends from another part of the tissue. The first suture end is held by the first and second holding structures so that there is a loose suture section between the first and second holding structures. The loose suture section is twisted about itself to define a loop. Preferably, a second instrument is twisted about its length to define the loop and is extendable therethrough in a first direction to grasp the second suture end. The second instrument, with the second suture end grasped thereby, is pulled in a second direction, opposite to the first direction, out of the loop. The first and second ends of the suture are then pulled apart to effect cinching thereof. Once the cinching is completed, the holding structures are operated to release the suture.

The instrument prevents the inadvertent pulling of the suture out of the tissue during the tying step by providing a stable support for the first suture end without tensioning the part of the suture that is extending through the tissue. At the same time, the loose section of the suture held by the instrument is conveniently positioned to allow the second instrument to loop the loose suture section about itself and grasp the second end in two very simple motions. In another application, the first suture end is held by the proximal releasably holding mechanism of the instrument of the invention and a second instrument is used to wrap the suture about the instrument of the invention, one or more times. Once this is accomplished the distal releasably holding mechanism is used to grasp the second suture end and pull it through the formed loop to cinch the half hitch.

In one form, the holding structure consists of a first cooperating pair of jaws with at least one of the jaws being movable by the actuating structure selectively a) towards the other of the jaws to place the first holding structure in a closed/holding position and b) away from the other of the jaws to place the first holding structure in an open/release position. In one preferred form, the second holding structure has the same general configuration as the first holding structure.

For convenience, the instrument body is elongate, with proximal and distal ends, and the first holding structure is adjacent the distal end, with the second holding structure disposed between the first holding structure and the proximal end of the body.

The jaws may take any of a number of different configurations. The jaws are, in one form, pivotable between the closed/holding and open/release positions for the jaw pairs. The jaws may both be movable or, alternatively, just one of the jaws is movable towards and away from the other jaw in its pair. With this arrangement, a fixed jaw can be provided on the body or the body itself can serve as the backing surface jaw for cooperation with the movable jaw.

Several different arrangements are contemplated by the invention for pivoting the jaw(s). The movable jaw can be pivoted relative to the body about a pin. The cooperating jaw can be fixedly attached to the body or an integral part thereof. In each case, the jaw can be biased normally towards a position in which the jaws are in their open/release positions.

In one form, the first actuating structure is a first handle that is movable relative to the body between first and second positions corresponding to closed/holding and open/release positions for the one jaw in the first jaw pair. The second actuating structure can have a second handle to effect operation of the second jaw pair in the same fashion.

In one form, the first and second handles are graspable by a single hand of a user and movable between their first, second, third and fourth positions.

In one form, the first and second actuating structure is a handle that is movable relative to the body between first, second and third positions. In the first handle position, each of the first and second holding structures is allowed to be placed in its open/release position. The handle in its second position causes only one of the first and second holding structures to be placed in its closed/holding position. In the third handle position, the handle causes both the first and second holding structures to be placed in their closed/holding positions.

The jaws are operable by any of a number of different mechanisms according to the invention. In one form, an elongate rod is movable relative to the body to effect movement of the jaws between closed/holding and open/release positions. Alternatively, a sleeve is movable relative to the body between first and second positions. In the first sleeve position, the one jaw is allowed to reside in its open/release position. With the sleeve in its second position, the sleeve squeezes the one jaw into its closed/holding position.

To facilitate operation of the handle(s), the handle is provided with a finger loop.

The present invention also comprehends an instrument for facilitating the tying of a suture and having a body with first structure on the instrument body for holding a first portion of a suture and second structure on the instrument body spaced from the first holding structure for holding a second portion of a suture.

In one form, the body has an elongate configuration with proximal and distal ends. There is a handle for holding the instrument at the proximal end of the body.

DETAILED DESCRIPTION OF THE DRAWINGS

Figure 1:
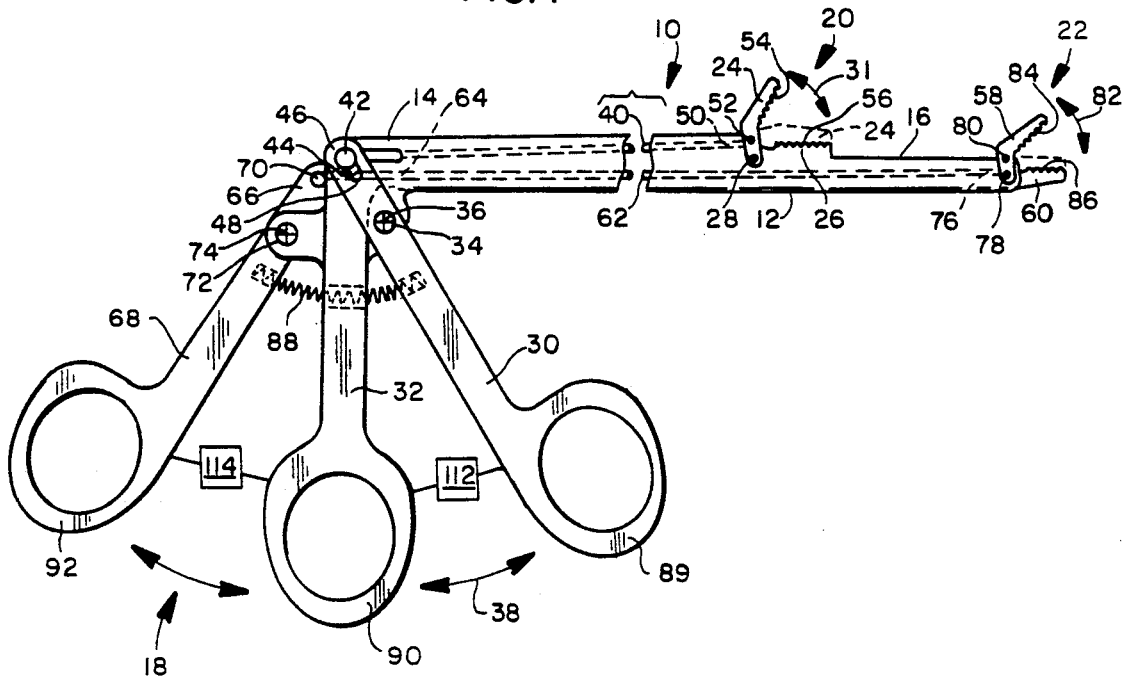
FIG. 1 is a side elevation view of an instrument for facilitating the tying of a suture according to the present invention and with spaced suture holding jaw pairs thereon both shown in an open position.
Figure 2:
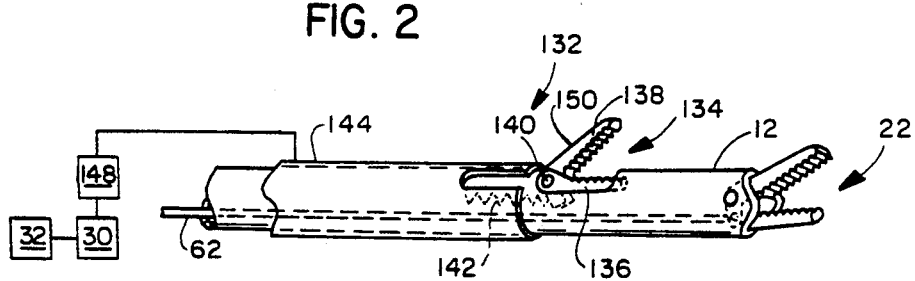
FIG. 2 is a fragmentary, perspective view of the distal end of an instrument with modified suture holding jaw pairs according to the invention and with the jaw pairs in a open/release position.
Figure 3:
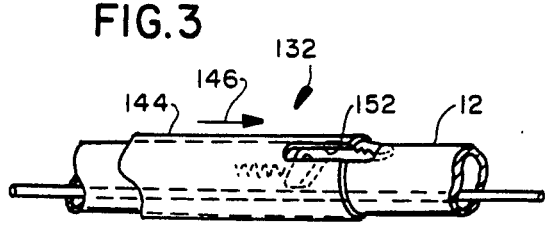
FIG. 3 is a view similar to that in FIG. 2 with one jaw pairs shown in a closed/holding position.
Figure 4:
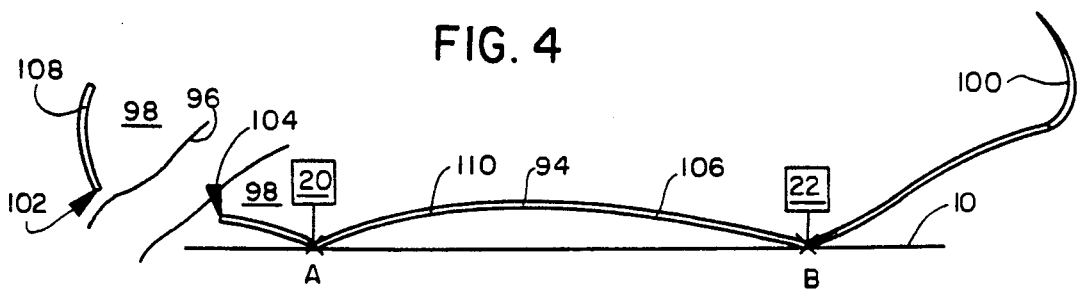
FIGS. 4–8 show the sequence of tying a suture according to the present invention using the instrument in FIGS. 1–3.

In FIG. 1, a preferred form of instrument for facilitating the tying of a suture, according to the present invention, is shown at 10. The instrument 10 consists of an elongate, hollow, cylindrical body 12 with axially spaced proximal and distal ends 14, 16, respectively. A handle/actuating mechanism is shown at 18 and is connected to the body 12 so as to define an overall L shape which can be held and operated in the manner of a pistol.

The instrument has first and second jaw pairs 20, 22 which are operated remotely by the handle/actuating mechanism 18. The first jaw pair 20 consists of a first, movable jaw 24 and a fixed jaw 26 that is integrally formed as one piece with the body 12. The jaw 24 is connected by a pin 28 for pivoting movement relative to the body 12 between the open/release position for the jaw pair 20, shown in solid lines in FIG. 1, and a closed/holding position therefor, shown in phantom lines in FIG. 1. A first handle 30 is movable to effect pivoting of the jaw 24 in the direction indicated by a double-headed arrow 31, between its open and closed positions.

More particularly, the body 12 has a depending, stationary handle 32 projecting perpendicular to the length of the body 12. A pin 34 connects the first handle 30 to the stationary handle 32 for pivoting movement about an axis 36 towards and away from each other, as indicated by the double-headed arrow 38.

The first handle 30 is pivotable to move an elongate, operating rod 40 in a fore and aft direction relative to the body 12. The operating rod 40 has a pin 42 projecting transversely to its length and into a slot 44 at the upper portion 46 of the first handle 30. With the instrument 10 in the FIG. 1 orientation, clockwise pivoting of the first handle 30 causes a forwardly facing surface 48 bounding the slot 44 to bear against the pin 42 to effect forward movement of the rod 40. The slot 44 permits a slight vertical shifting of the pin 42 during this motion to prevent binding between the handles 30, 32.

The forward end 50 of the rod 40 is pivotably connected by a pin 52 to the jaw 24 at a point above the pivot pin 28 for the jaw 24. Alternatively, the forward end 50 would be attached directly to pivot pin 28 to activate jaw 24. Forward movement of the rod 40 drives the jaw 24 in a clockwise direction around the pin 28 from the open position to its closed position, shown in phantom lines in FIG. 1. With the jaw pair 20 closed, teeth 54 on the jaw 24 mesh with teeth 56 on the fixed jaw 26 to allow positive gripping of a suture.

The second jaw pair 22 consists of a movable jaw 58 and a jaw 60 that is fixed at the free distal end 16 of the body 12. The movable jaw 58 is pivotable by an elongate operating rod 62 which extends lengthwise through the cylindrical body 12. The rear end 64 of the rod 62 is connected to the upper portion 66 of a second handle 68 through a pivot pin 70. The second handle 68 is in turn pivotably connected to the stationary handle 32 by a pin 72 for rotation about an axis 74 that is parallel to the pivot axis 36 for the handle 30.

The forward end 76 of the rod 62 is connected by a pin 78 to a bottom portion of the jaw 58. The jaw 58 is pivotably connected to the body 12 above the pin 78 by a separate mounting pin 80, which allows the jaw 58 to pivot from its open/release position, shown in solid lines in FIG. 1, to its closed/holding position, shown in phantom lines in FIG. 1, as indicated by the double-headed arrow 82. Pivoting of the second handle 68 in a counterclockwise direction about the pin 72 draws the rod 62 rearwardly, which imparts a clockwise pivoting movement to the jaw 58 to effect closing thereof. The jaw 58 has teeth 84 thereon which mesh with teeth 86 on the jaw 60, which is fixed to the body 12. It can be seen that the jaw pair 22 is conveniently located at the forwardmost part of the instrument 10 to facilitate pickup of an item to be held by the jaw pair 22.

A coil spring 88 is guided through the stationary handle 32 and biases the handles 30, 68 away from each other and the stationary handle 32. Consequently, the instrument 10 is normally maintained in a state wherein both jaw pairs 20, 22 are open, as shown in FIG. 1.

The operator can selectively close the first jaw pair 20 by placing fingers through loops 89, 90 on the handles 30, 32 and drawing the handle 30 towards the handle 32 in the manner that one closes a scissors. Alternatively, the user can operate the jaw pair 22 by placing fingers through a loop 92 on the handle 68 and the loop 90 on the handle 32 and squeezing the handle 68 towards the handle 32 against the bias of spring 88. The operator has the third option of simultaneously closing the jaw pairs 20, 22 by extending fingers through the grips 88, 92 and squeezing the handles 30, 68 towards each other and the stationary handle 32.

One particular application of the instrument 10 is shown in FIGS. 4-8, wherein a knot is tied in a suture 94 with the assistance of the instrument 10. The instrument 10 is shown schematically in FIGS. 4-8, as are the jaw pairs 20, 22. The suture 94 is used to close an incision 96 in a tissue 98.

The suturing process is initiated by directing a needle 100 through the tissue 98 at a location 102, on one side of the incision 96, and out through the tissue 98 at a second location 104 on the other side of the incision 96. The first suture end 106 is drawn through the tissue 98 to leave a second, trailing end 108, of a shorter length. With the instrument 10, the suture 94 is grabbed at spaced locations A, B, by the jaw pairs 22, 20, respectively. This positively grips the suture 94 and maintains a loose section 110 between the jaw pairs 20, 22. The invention contemplates that ratchets or locks 112, 114, of a type known to those skilled in the art, might be used to lock the handle 30 relative to the handle 32 and the handle 68 relative to the handle 32, respectively, to thereby maintain one or both of the jaw pairs 20, 22 in a closed position This obviates the user's having to maintain a pressure on the handles 30, 68 during the tying process.

Figure 5:
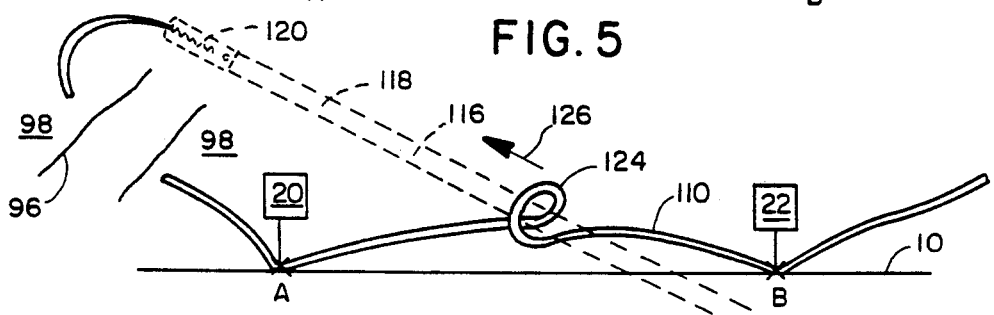
Figure 6:
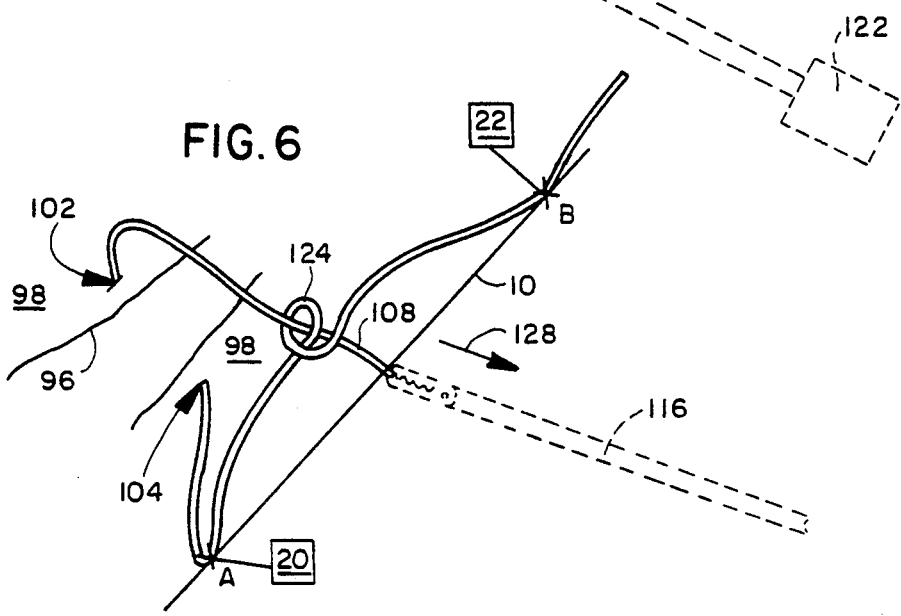
Figure 7:
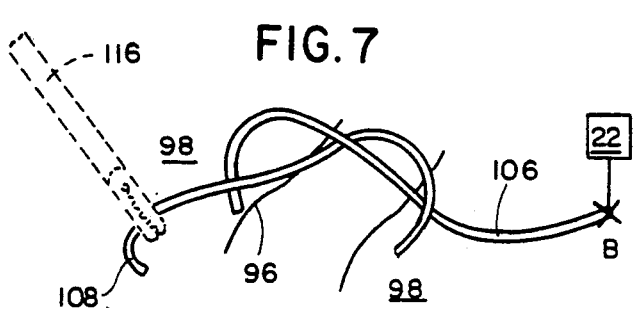
Figure 8:
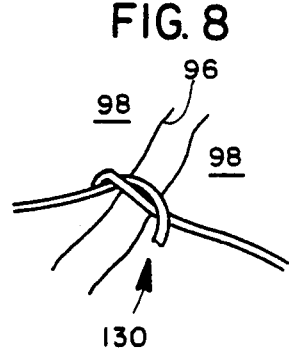

A second instrument 116 is provided and has an elongate body 118 and a pair of closeable jaws 120 operable through an actuating mechanism 122, shown schematically in FIG. 5. The user places the forward portion of the body 118 against the loose suture section 110 and then twists the section 110 about its length to define a loop 124 in the suture 94 as shown in FIG. 5. The instrument 116 is then advanced in a first direction, indicated by arrow 126, through the loop 124 until the jaws 120 can grasp the trailing suture end 108. The instrument 10 is repositioned as shown in FIG. 6 and at the same time the suture end 108 is drawn in the direction of arrow 128 out through the loop 124. The suture ends 106, 108 are then drawn against each other, as shown in FIG. 7, to complete the half-hitch, shown at 130 in FIG. 8.

It can be seen that the loose suture section 110 is held positively by the jaw pairs 20, 22 to allow formation of the loop 124 without any tendency of the trailing end 108 of the suture 94 to be drawn out of the tissue 98. At the same time, the suture 94 is held positively by two different jaw pairs 20, 22 operable by a single hand, which thus frees the user's other hand to complete the tying operation.

Variations of the basic instrument 10 are shown in FIGS. 2, 3 and 9-12. A first modification is incorporated into the instrument shown at 132 in FIGS. 2 and 3. Corresponding parts in the instrument 132 and that 10 in FIG. 1 will be numbered the same herein. The instrument 132 has a body 12 with a jaw pair 22 that is operable through a rod 62 as with the instrument 10. The principal distinction between the instrument 132 and that 10 in FIG. 1 resides in the jaw pair 134. The jaw pair 134 consists of a jaw 136 that is fixed to the body 12 and a jaw 138 that is connected by a pin 140 for pivoting movement towards and away from the jaw 136 between the open/release position shown in FIG. 2 and the closed/holding position shown in FIG. 3. A compression coil spring 142 normally urges the jaw 138 in a counterclockwise direction about the pin 140 to its open position in FIG. 2.

Closing of the jaw pair 134 is effected by an outer sleeve 144 which surrounds and is guided lengthwise against and relative to the body 12. Forward movement, i.e. to the right as indicated by arrow 146 in FIG. 3, of the sleeve 144 is accomplished by a mechanism shown schematically at 148, operatively associated with the handle 30, also shown schematically in FIG. 2. By squeezing the handle 30 towards the handle 32, the sleeve 144 is driven forwardly to cause a ramped surface 150 on the jaw 138 to encounter and thereby progressively cam the jaw 138 towards the closed position of FIG. 3. A cut-out 152 is provided in the sleeve 144 to prevent interference of the sleeve 144 with the pivot mechanism for the jaw pair 134. The instrument 132 otherwise operates in the same fashion as the instrument 10 previously described.

Figure 9:
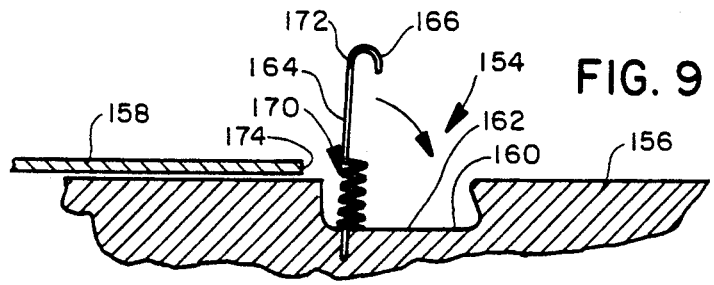
FIG. 9 is a fragmentary side elevation view of an alternative form of suture holding jaw pair according to the invention, with the jaw pair in an open/release position.
Figure 10:
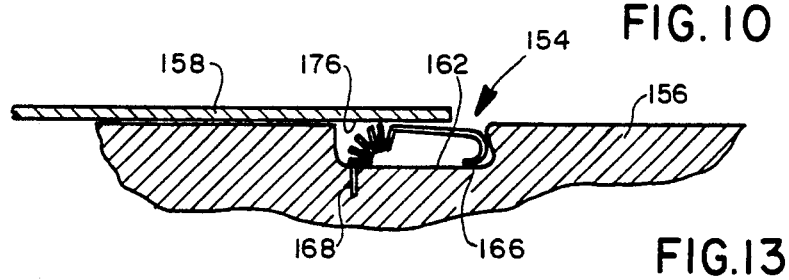
FIG. 10 is a view as in FIG. 9 with the jaw pair in a closed/holding position.

FIGS. 9 and 10 show a still further modified form of jaw pair at 154 useable with a cylindrical body 156 and slidable sleeve 158, corresponding to the body 12 and sleeve 144 in the instrument 132. The body 156 has a cut-out 160 with a stationary surface 162 operable as a stationary jaw. A pivotable jaw 164 has a grasping surface 166 to bear against the jaw surface 162.

The pivotable jaw 164 is defined by a formed wire. The jaw 164 has a root 168 embedded in the body 156, is wrapped to define a coiled section 170 and terminates in a J-shaped end 172. Upon the sleeve 158 advancing from left to right in FIGS. 9 and 10, the leading edge 174 thereof encounters the jaw 164 and bends the coiled section 170 to pivot the J-shaped end 172 in a counterclockwise direction from the open position shown in FIG. 9 into the cut-out 160 and the closed position shown in FIG. 10, wherein the jaw surface 166 facially abuts the jaw surface 162. The inside surface 176 of the sleeve 158 exerts a bias on the jaw 164 in its closed position to thereby slightly deform the end 172 of the jaw 164 and maintain a firm grasp on a suture captively held between the jaw 164 and the surface 162.

Figure 11:
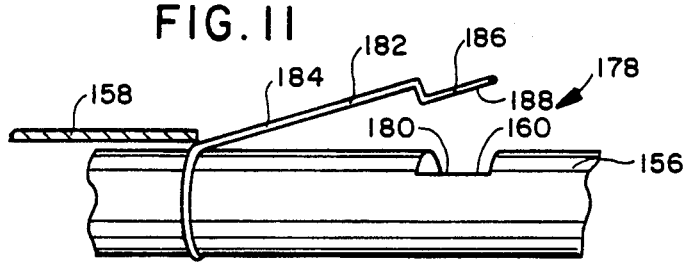
FIG. 11 is a view as in FIGS. 9 and 10 with a modified form of jaw pair according to the present invention, with the jaw pair shown in an open/release position.
Figure 12:
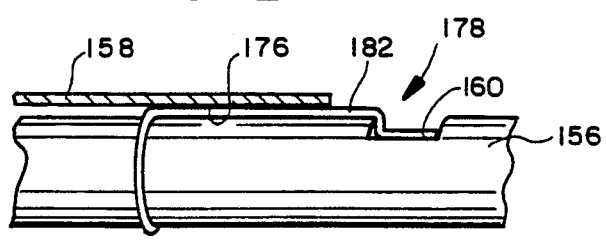
FIG. 12 is a view as in FIG. 11 with the jaw pair in a closed/holding position.

A modified form of jaw pair is shown at 178 in FIGS. 11 and 12. Corresponding parts in the jaw pairs 154 in FIGS. 9 and 10 and the jaw pair 178 in FIGS. 11 and 12 are numbered the same. The body 156 has a cut-out 160 defining a jaw surface 180 to cooperate with a movable jaw 182 integrally formed as one piece with the body 156 and projecting angularly upwardly therefrom in its normal state, in which the jaw pair 178 is in its open/release position. The jaw 182 has a main body 184 and an offset end 186 defining a surface 188 which facially abuts the jaw surface 180 to capture a suture therebetween. Left to right movement of the sleeve 158 progressively cams the jaw 182 from the FIG. 11 position to the closed/holding position for the jaw pair 178 in which the jaw surface 188 is against the body jaw surface 180. The inside surface 176 of the sleeve 158 maintains a constant pressure on the jaw 182 in its closed position of FIG. 12 to biasably urge the offset end 186 against the jaw surface 180 to firmly grasp the suture, as does the jaw pair 154 in FIGS. 9 and 10.

Figure 13:
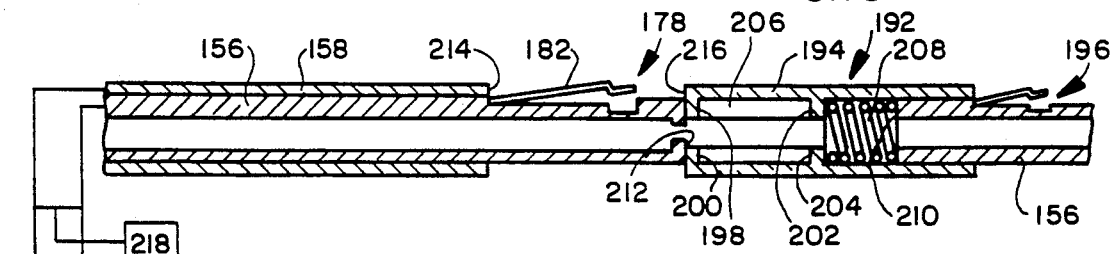
FIG. 13 is a cross-sectional view of a modified form of instrument for facilitating the tying of a suture according to the invention.

In FIG. 13, a modified form of instrument is shown at 192. The instrument 192 has several common features to that in FIGS. 11 and 12, and corresponding parts are numbered the same. The body 156 has a surrounding sleeve 158 to operate a jaw pair 178 by movement of the sleeve 158 from left to right through pivoting of a handle 68 relative to a stationary handle 32. This left to right movement of the sleeve 158 causes the movable jaw 182 to change from the open position of FIG. 10 to a closed position, corresponding to that for the jaw 182 in FIG. 12.

The instrument 192 has a second sleeve 194, forwardly of the sleeve 158, that operates a second jaw pair 196 in the same fashion as the jaw pair 178 is operated by the sleeve 158. The second sleeve 194 has lugs 198, 200, 202, 204 which move guidingly in a through slot 206 in the body 156. A coil spring 208 acts between a rearwardly facing shoulder 210 on the body 156 and the forwardmost lugs 202, 204 on the sleeve 194 to thereby urge the sleeve 194 rearwardly until the lugs 198, 200 abut an annular shoulder 212 on the body 156. The spring 208 thus normally biases the sleeve 194 to the FIG. 10 position in which the jaw pair 196 is open.

By urging the handle 68 towards the handle 32 in operation, the sleeve 158 is advanced from left to right in FIG. 13 to initially close the jaw pair 178. By continuing to advance the sleeve 158 through the handle 68, the forward edge 214 of the sleeve 158 encounters a rearwardly facing edge 216 on the sleeve 194 to thereby advance the sleeve 194 forwardly against the bias of the spring 208 to thereby close the jaw pair 196. An optional lock 218 can be used to maintain the handles 68, 32 in fixed relationship with the jaw pairs 178, 196 closed.

It can be seen that a single movement of the handle 68 towards the handle 32 effects first closing of the jaw pair 178 and then the jaw pair 196. This obviates the need for a second movable handle to further add to the convenience of the user.

The foregoing disclosure of specific embodiments is intended to be illustrative of the broad concepts comprehended by the invention.

we claim:

1. An instrument for facilitating the tying of a suture during a surgical procedure, said instrument comprising:
   an elongate body;
   first means at a first location on the body for holding a first portion of a suture at said first location; and
   second means at a second location on the body spaced lengthwise relative to the body from the first holding means for holding a second portion of a suture at said second location.

2. The instrument for facilitating the tying of a suture according to claim 1 wherein said first holding means includes a first cooperating pair of jaws movable relatively between an open/release position and a closed/holding position.

3. The instrument for facilitating the tying of a suture according to claim 2 wherein said second holding means includes a second cooperating pair of jaws movable relatively between an open/release position and a closed/holding position.

4. The instrument for facilitating the tying of a suture according to claim 3 including means remote from at least one of the first and second holding means for selectively placing the one of the first and second holding means in its open/release position and its closed/holding position.

5. An instrument for facilitating the tying of a suture during a surgical procedure, said instrument comprising:
   an elongate body;
   first means at a first location on the body for releasably holding a first portion of a suture at said first location;
   second means at a second location on the body spaced lengthwise relative to the body from the first holding means for releasably holding a second portion of a suture at said second location;
   first means on the body for actuating the first holding means to selectively cause the first holding means to hold and release a first portion of a suture at said first location; and
   second means on the body for actuating the second holding means to selectively cause the second holding means to hold and release a second portion of a suture at said second location.

6. The instrument for facilitating the tying of a suture according to claim 5 wherein the first suture holding means comprises a first cooperating pair of jaws with at least one of the jaws in the first jaw pair being movable by said first actuating means selectively a) towards the other of the jaws in the first jaw pair to place the first holding means in a closed/holding position and b) away from the other of the jaws in the first jaw pair to place the first holding means in an open/release position.

7. The instrument for facilitating the tying of a suture according to claim 6 wherein the second suture holding means comprises a second cooperating pair of jaws with at least one of the jaws in the second jaw pair being movable by said second actuating means selectively a) towards the other of the jaws in the second jaw pair to place the second holding means in a closed/holding position and b) away from the other of the jaws in the second jaw pair to place the second holding means in an open/release position.

8. The instrument for facilitating the tying of a suture according to claim 7 wherein the first actuating means comprises a first handle that is movable relative to the body between first and second positions corresponding to closed/holding and open/release positions for the one jaw in the first jaw pair.

9. The instrument for facilitating the tying of a suture according to claim 8 wherein the second actuating means comprises a second handle that is movable relative to the body between third and fourth positions corresponding to closed/holding and open/release positions for the one jaw in the second jaw pair.

10. The instrument for facilitating the tying of a suture according to claim 9 wherein the first and second handles are graspable by a single hand of a user and movable by a user's hand between their first, second, third and fourth positions.

11. The instrument for facilitating the tying of a suture according to claim 9 wherein the first and second handles are pivotable relative to the body and selectively towards and away from each other to operate the first and second holding means.

12. The instrument for facilitating the tying of a suture according to claim 11 wherein at least one of the first and second handles has a loop to allow grasping thereof by the finger of a user to facilitate manipulation of the one of the first and second handles.

13. The instrument for facilitating the tying of a suture according to claim 8 wherein the first handle is pivotable relative to the body between its first and second positions.

14. The instrument for facilitating the tying of a suture according to claim 6 wherein one of the jaws in the first jaw pair is in fixed relationship to the body.

15. The instrument for facilitating the tying of a suture according to claim 6 wherein one of the jaws in the first jaw pair is integrally formed with the body.

16. The instrument for facilitating the tying of a suture according to claim 6 wherein the at least one movable jaw is pivotable between its closed/holding and open/release positions.

17. The instrument for facilitating the tying of a suture according to claim 16 wherein said first actuating means includes an elongate rod movable relative to the body to effect movement of the one movable jaw between its closed/holding and open/release positions.

18. The instrument for facilitating the tying of a suture according to claim 16 wherein the one movable jaw defines a flexible coil that allows the one movable jaw to pivot between its closed/holding and open/release positions.

19. The instrument for facilitating the tying of a suture according to claim 6 wherein one of said jaws is deformable to allow it to be pressed against the other jaw and deformed to exert a bias on a suture held captively between said jaws.

20. The instrument for facilitating the tying of a suture according to claim 5 wherein the instrument body is elongate and has a proximal end and a distal end, the first holding means is adjacent the distal end of the body and the second holding means is disposed between the first holding means and the proximal end of the body.

21. An instrument for facilitating the tying of a suture during a surgical procedure, said instrument comprising:
a body;
first means on the body for releasably holding a first portion of a suture;
second means on the body spaced from the first holding means for releasably holding a second portion of a suture;
first means on the body for actuating the first holding means to selectively cause the first holding means to hold and release a first portion of a suture; and
second means on the body for actuating the second holding means to selectively cause the second holding means to hold and release a second portion of a suture,
wherein the first suture holding means comprises a first cooperating pair of jaws with at least one of the jaws in the first jaw pair being movable by said first actuating means selectively a) towards the other of the jaws in the first jaw pair to place the first holding means in a closed/holding position and b) away from the other of the jaws in the first jaw pair to place the first holding means in an open/release position,
wherein the second suture holding means comprises a second cooperating pair of jaws with at least one of the jaws in the second jaw pair being movable by said second actuating means selectively a) towards the other of the jaws in the second jaw pair to place the second holding means in a closed/holding position and b) away from the other of the jaws in the second jaw pair to place the second holding means in an open/release position,
wherein the first and second actuating means include a handle that is movable relative to the body between first, second and third positions, said first and second actuating means including first cooperating means operable by said handle and connected with the first and second pair of jaws for moving the first and second pairs of jaws between their open/release position and closed/holding position in response to movement of the handle such that with a) said handle in said first position each of said first and second holding means is place in its open/release positions, b) said handle in its second position only one of the first and second holding means is placed in its closed/holding position by said first cooperating means and c) said handle in its third position both the first and second holding means are place in their closed/holding positions by the first cooperating means.

22. An instrument for facilitating the tying of a suture during a surgical procedure, said instrument comprising:
body;
first means on the body for releasably holding a first portion of a suture;
second means on the body spaced from the first holding means for releasably holding a second portion of a suture;
first means on the body for actuating the first holding means to selectively cause the first holding means to hold and release a first portion of a suture; and
second means on the body for actuating the second holding means to selectively cause the second holding means to hold and release a second portion of a suture, wherein the first suture holding means comprises a first cooperating pair of jaws with at least one of the jaws in the first jaw pair being movable by said first actuating means selectively a) towards the other of the jaws in the first jaw pair to place the first holding means in a closed/holding position and b) away from the other of the jaws in the first jaw pair to place the first holding means in an open/release position, wherein said one movable jaw is normally in its open/release position and the first actuating means includes a sleeve that is movable relative to the body between first and second positions, said sleeve in its first position allowing the one movable jaw to reside in its open/release position, and said sleeve in its second position squeezing the one movable jaw into its closed/holding position.

23. An instrument for facilitating the tying of a suture during a surgical procedure, said instrument comprising:

an elongate body;

first means at a first location on the body for releasably holding a first portion of a suture at said first location;

second means at a second location on the body spaced lengthwise relative to the body from the first holding means for releasably hold a second portion of a suture at said second location;

first means on the body for actuating the first holding means to selectively cause the first holding means to hold and release a first portion of a suture at said first location; and second means on the body for actuating the second holding means to selectively cause the second holding means to hold and release a second portion of a suture at said second location, wherein the first suture holding means comprises a first cooperating pair of jaws with at least one of the jaws in the first jaw pair being movable by said first actuating means selectively a) towards the other of the jaws in the first jaw pair to place the first holding means in a closed/holding position and b) away from the other of the jaws in the first jaw pair to place the first holding means in an open/release position, wherein the at least one movable jaw is pivotable between its closed/holding and open/release positions, wherein the one movable jaw is integrally formed as one piece with the body.

24. An instrument for facilitating the tying of a suture during a surgical procedure, said instrument comprising:

an elongate body.

first means on the instrument body for holding a first portion of a suture; and second means on the instrument body spaced from the first holding means for holding a second portion of a suture, said first holding means including a first cooperating pair of jaws movable relatively between an open/release position and a closed/holding position about a first axis that is fixed relative to the body, said second holding means including a second cooperating pair of jaws movable relatively between an open/release position and a closed/holding position about a second axis that is fixed relative to the body, said second axis being spaced lengthwise of the body relative to the first axis.

25. An instrument for facilitating the tying of a suture during a surgical procedure, said instrument comprising:

a body;

first means on the body for releasably holding a first portion of a suture;

second means on the body spaced from the first holding means for releasably holding a second portion of a suture;

first means on the body for actuating the first holding means to selectively cause the first holding means to hold and release a first portion of a suture; and second means on the body for actuating the second holding means to selectively cause the second holding means to hold and release a second portion of a suture, wherein the first suture holding means comprises a first cooperating pair of jaws with at least one of the jaws in the first jaw pair being movable by said first actuating means selectively a) towards the other of the jaws in the first jaw pair to place the first holding means in a closed/holding position and b) away from the other of the jaws in the first jaw pair to place the first holding means in an open/release position, wherein the one movable jaw comprises a flexible element that is moved by the first actuating means between its open/release position and closed/holding position solely by bending of the one movable jaw.

26. A method of tying a suture that extends through a tissue and has a first end extending from one part of the tissue and a second extending from another part of the tissue, said method comprising the steps of:

providing an instrument with first and second spaced means for holding separate portions of a suture;

holding the first suture end with said first and second holding means so that there is a loose suture section between the first and second holding means;

twisting the loose suture section about itself to define a loop;

extending a second instrument in a first direction through the loop;

grasping the second suture end with the second instrument;

pulling the second suture end in a second direction that is opposite to said first direction out of said loop with said second instrument;

releasing the first suture end from one of the first and second holding means; and pulling the first and second ends of the suture apart from each other to cinch the suture.

27. The method of tying a suture according to claim 26 including the step of forming the loop with said second instrument by engaging the second instrument with the loop suture section and repositioning the second instrument to thereby define said loop.

28. The method of tying a suture according to claim 26 including the step of releasing the suture from each of the first and second holding means after the suture is cinched.

* * * * *